US008344122B2

(12) United States Patent
Toriyama et al.

(10) Patent No.: US 8,344,122 B2

(45) Date of Patent: Jan. 1, 2013

(54) FERTILITY RESTORER GENE AND FERTILITY RESTORATION METHOD FOR CW-TYPE MALE STERILE CYTOPLASM OF RICE

(75) Inventors: Kinya Toriyama, Sendai (JP); Sota Fujii, Sendai (JP)

(73) Assignee: Tohoku University, Sendai-Shi Miyagi (JP)

( * ) Notice: Subject to any disclaimer, the term of this patent is extended or adjusted under 35 U.S.C. 154(b) by 0 days.

(21) Appl. No.: 12/922,071

(22) PCT Filed: Feb. 21, 2009

(86) PCT No.: PCT/JP2009/000753

§ 371 (c)(1), (2), (4) Date: Nov. 18, 2010

(87) PCT Pub. No.: WO2009/113249

PCT Pub. Date: Sep. 17, 2009

(65) Prior Publication Data

US 2011/0060033 A1 Mar. 10, 2011

(30) Foreign Application Priority Data

Mar. 12, 2008 (JP) ................................ 2008-062879

(51) Int. Cl.
*C07H 21/04* (2006.01)
*C12P 19/34* (2006.01)

(52) U.S. Cl. .................................. 536/24.33; 435/6.12

(58) Field of Classification Search ........................ None
See application file for complete search history.

(56) References Cited

U.S. PATENT DOCUMENTS

| | | | |
|---|---|---|---|
| 2004/0123343 | A1 | 6/2004 | Barbazuk et al. |
| 2006/0123505 | A1 | 6/2006 | Kikuchi et al. |
| 2007/0020621 | A1 | 1/2007 | Boukharov et al. |

OTHER PUBLICATIONS

GenBank Accession No. AL731582, (2002).*
Stratagene 1988 catalog index.*
GTAAAC recogntion site enzymes list generated Apr. 2012.*
Maelll recogntiion site generated Apr. 2012.*
Fuji and Toriyama. Suppressed expression of Retrograde-Regulated Male Sterility restores pollen fertility in cytoplasmic male sterile rice plants. PNAS 106(23):9513-9518, Jun. 2009.*
Extended European Search Report, European Patent Office, Germany, EPO Form 1507S of International Application No. PCT/JP2009000753.
Sota Fujii, et al: "Retrograde regulation of nuclear gene expresion in CW-CMS of rice." Plant Molecular Biology, Kluwer Academic Publishers, Dordrech, NL, vol. 63, No. 3, Nov. 4, 2006, pp. 405-417, XP019483635, ISSN: 1573-5028.
Zabaleta Eduardo, et al: "Transgenic male-sterile plain induced by an unedited atp9 gene is restored to fertility by inhibiting its expression with antisense RNA." Proceedings of the National Academy of Sciences of the United States of America, vol. 93, No. 20, 1996, pp. 11259-11263, XP002619119, ISSN: 0027-8424, DOI: http://dx.doi.org/10.1073%2Fpnas.93.20.11259.
Sota Fujii, et al: "Molecular mapping of the fertility restorer gene for ms-CW-type cytoplasmic male sterility of rice." Theoretical and Applied Genetics; International Journal of Plant Breeding Research, Springer, Berlin, DE, vol. 111, No. 4, Aug. 1, 2005, pp. 696-701, XP019 322012, ISSN: 1432-2242, DOI:10.1007/500122-005-2054-0.
Chase et al: "Cytoplasmic male sterility: a window to the world of plant mitochondrial-nuclear interactions." Trends in Genetics, Elsevier Science Publishers B.V. Amsterdam, NL, vol. 23, No. 2, Jan. 30, 2007, pp. 81-90, XP005864360, ISSN: 0168-9525, DOI:DOI: 10.1016/J. TIG.2006.12.004 p. 87, col. 2, line 6-line 22.
Fujii, s., et al., Retrograde Regulation of Nuclear Gene Expression in CW-CMS of Rice; Plant Molecular Biology, 2007, Vo. 63, pp. 405-417.
International Search Report, Mar. 9, 2009 in counterpart foreign application under the WIPO, Application No. PCT/JP2009/000753.

* cited by examiner

*Primary Examiner* — Samuel Woolwine
*Assistant Examiner* — Suchira Pande
(74) *Attorney, Agent, or Firm* — Andrews Kurth, LLP; Michael Ye

(57) ABSTRACT

Mainly provided is a technique for directly identifying the genotype at locus Rf17 based on the specific base sequence data thereof. Also provided is a technique for artificially constructing a fertility-restored line. A method of restoring the fertility of CW-type cytoplasmic male sterile rice by inhibiting or reducing the expression of a gene comprising the base sequence represented by SEQ ID NO:2 in the above-described rice, and a method for determining the presence or absence of gene Rf17, which is a fertility restorer gene for CW-type cytoplasmic male sterility, comprising identifying a single nucleotide polymorphism (SNP) in the base at the 1812 position of the base sequence represented by SEQ ID NO:1 in the rice to be examined.

6 Claims, 3 Drawing Sheets

FERTILITY RESTORER GENE AND FERTILITY RESTORATION METHOD FOR CW-TYPE MALE STERILE CYTOPLASM OF RICE

The present invention relates to a method for restoring the fertility of CW-type cytoplasmic male sterile rice, and to a method for determining the presence or absence of a fertility restorer gene and the like. Cytoplasmic Male Sterility (referred to hereinafter as "CMS") means that the formation of pollen having the ability to germinate is inhibited due to mutation in a mitochondrial gene so that a seed will develop into seeds. It is known that fertility can be restored by the function of a pollen fertility restorer gene (Rf) encoded in a nuclei in some cases of CMS.

BACKGROUND

A method for breeding a first filial generation is also called a method for breeding of a hybrid-variety. This method is utilized in variety-breeding since a variety having excellent traits inherited from its parents and showing heterosis hybrid vigour can be bred by means of this method. In order to economically harvest F1 hybrid seeds in large quantity, a three-line method utilizing cytoplasmic male sterility is adopted in the case of seed-harvesting of a hybrid variety of rice. The three-line method refers to a method that utilizes a sterile line having male sterility, a fertility restorer line, and a maintainer line having the same nuclear genes as the sterile line but not having sterile cytoplasm. According to this three-line method, (1) a hybrid seed can be harvested by crossing the sterile line with pollen of the restorer line, while (2) the sterile line can be maintained by crossing the sterile line with the pollen of the maintainer line.

BT-type male sterile cytoplasm and WA-type male sterile cytoplasm have been used worldwide in order to breed the hybrid variety with the three-line method. On the other hand, CW-type male sterile cytoplasm has been hardly utilized since the structure and function of a fertility restorer gene Rf17 (Non Patent Document 1) have not been clarified. However, since there may be a risk of variety collapse due to limit in the genetic resources provided by the male sterile cytoplasm that have been used until now, utilization and development of novel male sterile cytoplasm are now desired.

In the prior arts, it has been necessary to breed plant body (F1) from a hybrid seed obtained by test cross, and then to make the F1 self-cross and to investigate frequency of appearance of a individual plant having seed-development rate over a certain level (for example, 90% or more) for the estimation of a genotype of Rf17 locus in the plant. It has not been possible to determine said genotype by means of DNA markers.

Non Patent Document 1: Sota Fujii and Kinya Toriyama (2005) Molecular mapping of the fertility restorer gene for ms-CW-type cytoplasmic male sterility of rice. Theor. Appl. Genet. 111:696-701

SUMMARY OF INVENTION

Problem to be Solved by the Invention

If the CW-type male sterile cytoplasm is utilized in the three-line method, it will be necessary to confirm that rice is holding Rf17 gene in each step of breeding the rice of the restorer-line, and that it holds Rf17 gene in both alleles at a final stage. It is therefore a main purpose of this invention to provide a technique to directly identify the genotype of Rf17 locus on the basis of its specific base sequence, and to provide a technique to artificially produce a fertility restorer line and the like.

Means for Solving the Problem

The present inventors have determined a base sequence comprising the fertility restorer gene Rf17 for the CW-type male sterile cytoplasm, which is represented by SEQ ID NO:1. We also have succeeded in the restoration of fertility of CW-type cytoplasmic male sterile rice by inhibiting the expression of a gene comprising the base sequence represented by SEQ ID NO:2, leading to the completion of the present invention.

Thus, the present invention relates to the following aspects:

1. A method for restoring the fertility of CW-type cytoplasmic male sterile rice, comprising inhibiting or reducing the expression of a gene comprising the base sequence represented by SEQ ID NO:2 in said rice.
2. The method according to claim 1, wherein the fertility is restored by introducing a genomic fragment into the CW-type cytoplasmic male sterile rice, wherein the fragment is derived from the chromosome No. 4 of a fertility restorer line for the CW-type cytoplasmic male sterility and comprises nucleic acids consisting of the base sequence of at least at the 1611-4835 positions of the base sequence represented by SEQ ID NO:1.
3. The method according to claim 2, wherein the genomic fragment consists of the whole base sequence represented by SEQ ID NO:1.
4. The method according to claim 1, wherein the fertility is restored by inhibiting the expression of the gene represented by SEQ ID NO:2 by means of RNA interference method.
5. The method according to claim 4, wherein the RNA interference is induced by introducing a vector comprising a gene consisting of the base sequence represented by SEQ ID NO:2 or a continuous 100-500-base sequence in its 3' non-translation region and their complementary sequence and expressing a double-stranded RNA that is capable of inducing the RNA interference in a cell into the CW-type cytoplasmic male sterile rice.
6. The method according to claim 5, which uses a vector comprising a continuous base sequence at the 638-815 positions of the base sequence represented by SEQ ID NO:2 and its complementary sequence and expressing a double-stranded RNA that is capable of inducing the RNA interference in a cell.
7. Rice whose fertility has been restored by the method according to any one of claims 1-5.
8. A method for breeding a first filial generation variety using the rice according to claim 7.
9. F1 hybrid seed harvested from the first filial generation variety bred by the method according to claim 8
10. A method for determining the presence or absence of gene Rf17, which is a fertility restorer gene for the CW-type cytoplasmic male sterility, comprising identifying a single nucleotide polymorphism (SNP) in a base at the 1812 position of the base sequence represented by SEQ ID NO:1 in rice to be examined.
11. The method according to claim 10, wherein the SNP is identified by means of CAPS method.
12. The method according to claim 11, which uses a restriction enzyme recognizing the cleavage site GT(A)AAC.
13. The method according to Claim 12, wherein the restriction enzyme is MaeIII.

14. A kit used for the method according to any one of claims 10-13.

Advantages of the Invention

The present invention has revealed that the CW-type male sterility is restored by the reduction of the expression of ORF11. And, the present inventors have succeeded in the identification of a base sequence that is effective in the restoration of the CW-type male sterility and in the restoration of said fertility

BEST MODE FOR CARRYING OUT THE INVENTION

Figure 1:
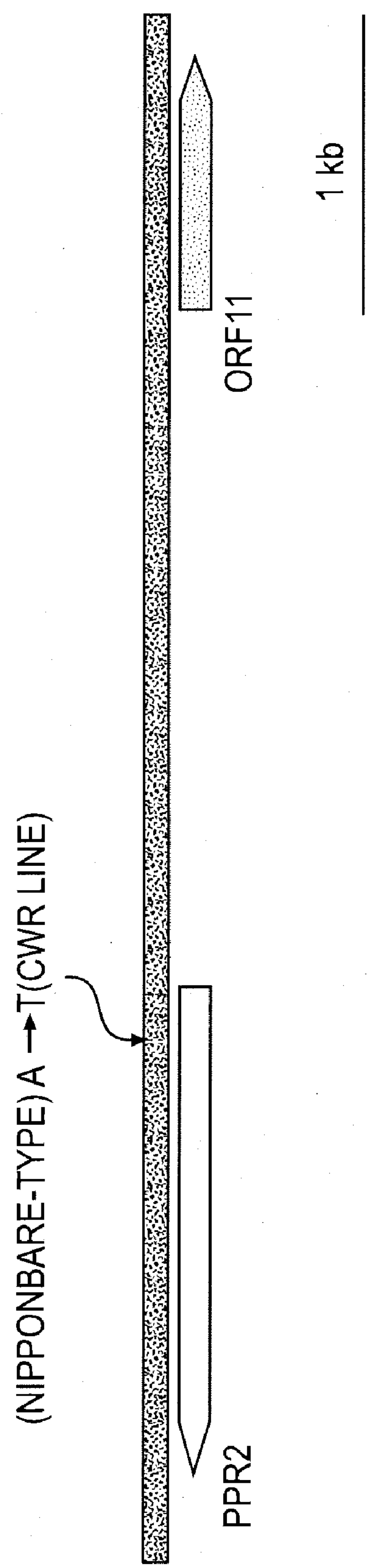
FIG. 1 A pattern diagrams showing a gene present in the gene fragments that restored fertility in a complementarity test.

The present inventors have succeeded in the determination of a genomic region comprising the fertility restorer gene Rf17 for the CW-type male sterile cytoplasm in the chromosome No. 4 of rice, which is represented by SEQ ID NO:1, by means of a conventional map-base cloning method. We also have further succeeded in the restoration of fertility of the CW-type cytoplasmic male sterile rice by inhibiting or reducing the expression of a gene (ORF11) represented by SEQ ID NO:2. The function of the gene represented by SEQ ID NO:2 has not yet known.

The map-base cloning method is also called a "chromosome walking", which focuses a genomic region in which a gene to be isolated exists by means of a DNA marker that is present in the vicinity of said gene. This method is used as one of isolation methods of a gene when the function or translation product of the gene can not estimated. Although this method has been utilized for the gene-isolation in some kinds of animals and plants, it is more effectively used in the plants from which a segregating population for laboratory use may be produced according to a plan. The genomic sequence of nipponbare-typc rice .http://rgp.dna.affrc.go.jp/J/index.html. was utilized in the map-base cloning according to the present invention.

The present inventors have found a way of introducing a genomic fragment into the CW-type cytoplasmic male sterile rice, wherein the fragment is derived from the chromosome No. 4 of a fertility restorer line for the CW-type cytoplasmic male sterility and comprises nucleic acids consisting of the base sequence of at least at the 1611-4835 positions of the base sequence represented by SEQ ID NO:1 in order to inhibit or reduce the expression of the gene comprising the base sequence represented by SEQ ID NO:2. The whole base sequence represented by SEQ ID NO:1 is listed as one of the examples of the above genomic fragments.

The examples of the above genomic fragment further include a nucleic acid which may hybridize with a nucleic acid consisting of the base sequence complementary with the base sequence represented by EQ ID NO:1 or its part under stringent conditions, and a nucleic acid consisting of the base sequence having homology of about 80% or more, preferably about 95% or more with the above nucleic acids. Those nucleic acids can restore the fertility of CW-type cytoplasmic male sterile rice.

The hybridization may be carried out by or according to a method known in the art such as, for example, Molecular cloning third. ed. (Cold Spring Harbor Lab. Press, 2001). Commercially available libraries may be used in accordance with the description of an attached instruction for use.

The "stringent conditions" in the present specification means, for example, the temperature of 60-68° C., sodium concentration of 150-900 mM, preferably 600-900 mM and pH6-8.

Accordingly, the above nucleic acid which may hybridize with a nucleic acid consisting of the base sequence complementary with the base sequence represented by EQ ID NO:1 or its part may be a nucleic acid comprising the base sequence having homology of about 80% or more, preferably about 95% or more, more preferably 99% or more with the whole base sequence of said nucleic acids.

The sequences may be pre-treated into a suitable state for comparison before homology (identity) is determined between two base- or amino acid-sequences. For example, a gap may be introduced into the sequence of one of them so as to optimize alignment with the other sequence. The amino acid or base sequences will be compared in each part thereof. When a part of the first sequence has the same amino acid or base sequence as a corresponding part of the second sequence, their sequences are deemed to be identical with each other in those parts. Homology between the two sequences is shown as a percentage of the number of the same amino acids or bases for the total number of the amino acids or bases in that part.

According to the above principle, homology (sequence homology) between two base sequences may be determined by means of algorism of Karlin and Altschul (Proc. Natl. Acad. Sci. USA 87:2264-2268.1990 and Proc. Natl. Acad. Sci. USA 90:5873-5877.1993). BLAST and FAST programs based on the above algorism are used to investigate a sequence having a high homology with a given sequence from data base. These programs are available in the website of the National Center for Biotechnology Information on the Internet.

The nucleic acid having the above homology in the base sequence may be obtained using hybridization as an index, or obtained from a group of unidentified DNAs that have been obtained by the analysis of genomic base sequences or from public database by using any method that those skilled in the art usually uses, such as BLAST software. The gene according to the present invention may also be obtained by a known mutation-introducing method.

The expression of the gene comprising the base sequence represented by SEQ ID NO:2 in the CW-type cytoplasmic male sterile rice may be inhibited or reduced by any other methods known for those skilled in the art. For example, the fertility of the CW-type cytoplasmic male sterile rice may be restored with anti-sense RNA method or by the inhibition of the expression of the gene represented by SEQ ID NO:2 with RNA interference method in accordance with the Example of the present specification.

Thus, the RNA interference may be induced by introducing a vector into the CW-type cytoplasmic male sterile rice, wherein the vector is designed to express a double-stranded RNA capable of inducing the RNA interference so as to inhibit or reduce the expression of the gene comprising the base sequence represented by SEQ ID NO:2. The vector includes one comprising a gene consisting of the base sequence represented by SEQ ID NO:2 or a continuous 100-500-base sequence, preferably a continuous 150-200-base sequence in its 3' non-translation region and their complementary sequence and expressing a double-stranded RNA that is capable of inducing the RNA interference in the cell. An example of said vector is one comprising a continuous 178-base sequence at the 638-815 positions of the base sequence represented by SEQ ID NO:2 (its first base is numbered as "1 position") and its complementary sequence and expressing a double-stranded RNA that is capable of inducing the RNA interference.

The above vector may be prepared by combining the above DNA with a vector according to any suitable gene-engineering technique known for those skilled in the art. The above vector may comprise a suitable promoter and any other controlling sequences, for example, enhancer, sequence, terminator sequence, polyadenylation sequence and the like in order to express the gene according to the present invention in a host cell.

The genomic region or the vector to be used for the inhibition or reduction of the expression of the gene comprising the base sequence represented by SEQ ID NO:2 in the CW-type cytoplasmic male sterile rice may be introduced into a subject rice by any method known for those skilled in the art such as *Agrobacterium* method, freeze-thaw method and electroporation method.

As a result, the fertility is restored in the CW-type cytoplasmic male sterile rice. Accordingly, a first filial generation variety is bred using the rice whose fertility has thus been restored so that an F1 hybrid seed can be harvested from the variety.

The present invention is further relates to a method for determining the presence or absence of a fertility restorer gene for the CW-type cytoplasmic male sterility, Rf17 or a genomic region comprising the gene, comprising identifying a single nucleotide polymorphism (SNP:A/T) in a base at the 1812 position of the base sequence represented by SEQ ID NO:1 in the rice to be examined.

The determination of SNP may be carried out by any method known for those skilled in the art, such as base sequence-determination method, SSCP (single strand conformation polymorphism) method, ASA (Allele specific amplification), primer extension method, Taqman method, invasion method, dot-blot-SNP Method, FRIP (Fluorogenic Ribonuclease Protection) method, and TILLING (Targeting Induced Local Lesion in Genome) method.

There is also CAPS (Cleaved Amplified Polymorphic Sequence) method for the above determination, as described in the Example of the present specification. In this method, a primer is so designed that a restriction enzyme-recognition site will be formed at a location where the SNP exists, followed by PCR-RFLP analysis on polyacrylamide gel. This method has an advantage that its results will hardly be affected by the conditions of an experimenter or a sample, or the kind of a DNA extraction method so as to easily obtain constant results. Furthermore, the method can be performed in a relatively simple way and does not need an expensive apparatus such as a DNA sequencer or advanced technique.

Primers, markers or probes that are used in the above method for the identification of SNP may be easily designed and prepared by those skilled in the art in accordance with the principles of each method on the basis of the database described above and the information about the DNA sequence of SEQ ID: NO 1 or NO:2 disclosed in the present specification. For example, a primer used in PCR of the CAPS method usually has the length of several tens of by such as 10-30 bp.

Various kinds of oligonucleotides that will be used as the above primers, markers or probes may be synthesized in vitro by any method known for those skilled in the art, such as chemical synthesis methods that are described, for example, in Carruthers 0.1982. Cold Spring Harbor Symp. Quant. Biol. 47:411-418; Adams. 1983. J. Am. Chem. Soc. 105:661; Belousov. 1997. Nucleic Acid Res. 25:3440-3444; Frenke 1.1995. Free Radic. Biol. Med. 19:373-380; Blommers. 1994. Biochemistry 33:7886-7896; Narang. 1979. Meth. Enzymol. 68:90; Brown. 1979. Meth. Enzymol. 68:109; Beaucage. 1981. Tetra. Lett. 22:1859; U.S. Pat. No. 4,458,066. Any known labeling substance may be attached to them for detection.

As a sample of rice to be examined, any part of the rice may be used such as its seed, leaf and stem. DNA may be extracted and prepared by any method known for those skilled in the art from the above sample. The kind of DNA to be prepared from the sample has no limitation, a genomic DNA (gDNA) and cDNA being listed for example. They may be extracted and purified by any method known for those skilled in the art depending on their properties, and kinds and properties of the sample. For example, gDNA may be obtained by CTAB method, boiling method and enzyme method using amylase or protease, if necessary.

If a sufficient amount the DNA is extracted from the sample rice for detection, it will be subjected to the following procedures without amplification. However, the DNA will be usually amplified to an amount suitable for the identification of SNP by means of any gene-amplification method known for those skilled in the art, such as PCR (Polymerase Chain Reaction) or RT-PCR method, ICAN (Isothermal and chimeric primer-initiated amplification of nucleic acids) method, NASBA (Nucleic acid sequence based amplification) method, TMA (Transcription-mediated amplification) method and SDA (Strand Displacement Amplification) method.

The present invention also relates to a kit used for the method for determining the presence or absence of gene Rf17. Depending on the kinds of SNP analysis and the like, the kit comprises primers, markers or probes for the identification of SNP. It may further optionally comprise various primer set and/or marker for the amplification of DNA, a restriction enzyme and other elements or components known for those skilled in the art such as, for example, various agents, enzymes, and buffer, a reaction plate (vessel) depending on its structure and purpose.

Although the present invention will be explained in more detail with reference to the following Examples, the technical scope of the present invention shall not be construed to be limited by them. The terms described in the present specification are used in such meaning as is usually used in the art unless particularly noted otherwise.

Unless otherwise described, each procedure may be carried out in accordance with standard techniques in gene engineering and molecular biology known for those skilled in the art, such as those described in Sambrook and Maniatis, in Molecular Cloning—A Laboratory Manual, Cold Spring Harbor Laboratory Press, New York, 1989; Molecular cloning third. ed. Cold Spring Harbor Lab. Press. 2001; Ausubel, F. M. et al., Current Protocols in Molecular Biology, John Wiley & Sons, New York, N.Y., 199 and the like. The content of the publications cited in the present specification will constitute a part of the disclosure of the present specification.

EXAMPLE 1

Restoration of the Fertility by Introduction of a Genomic Fragment of the Base Sequence Represented by SEQ ID NO:1

Mapping of Rf11 using the fertility restorer line (CWR line) for the CW-type CMS line revealed that Rf17 exists in a region of 77 kb of the chromosome No. 4, so that the base sequence of that region was determined. The genomic region was divided into seven fragments and subjected to sub-cloning Each genomic fragment was then introduced into the CW-type CMS line by means of *Agrobacterium* method and the seed fertility of the transformed plant was investigated. A plant individual whose fertility had restored was obtained from the plant transformed with the genomic fragment No. 5 (Table. 1). Fertility was restored in four (4) individuals among 44 re-differentiation lines. The four individuals showed the seed fertility of 79.3, 23.1, 25.3 and 68.1%, respectively. The base sequence of the fragment No. 5 is shown as SEQ ID NO:1.

TABLE 1

| No. of Gene Introduction | No. of Individuals of Re-differentiation | No. of Individuals of Fertility Restoration |
|---|---|---|
| 1 | 17 | 0 |
| 2 | 9 | 0 |
| 3 | 8 | 0 |
| 4 | 10 | 0 |
| 5 | 44 | 4 |
| 6 | 7 | 0 |
| 7 | 6 | 0 |

Two genes were predicted in the above fragment, which were PPR gene and a functionally unidentified gene (named as "ORF11") (FIG. 1). The comparison in expression between the CMS line and the fertility restored line revealed that the expression of ORF11 was high in the CMS line but low in the fertility-restored line, while there is no difference in the expression of PPR gene between them. The reduction of the expression of ORF11 was also observed in the next generation of the transformation line whose fertility had been restored. The comparison of base sequence between the CMS line and the fertility-restored line showed that there was a single base-substitution within the PPR gene, which generated a stop codon in the fertility-restored line (FIG. 1). As the single base-substitution was located 5'-upstream of ORF11, it was considered that the expression of ORF11 was reduced in the fertility-restored line due to the above mutation. It was therefore concluded that the fertility was restored due to the reduction of the expression of ORF11. Accordingly, it has been revealed that the fertility is restored by introducing a genomic fragment comprising the base sequence represented by SEQ ID NO:1, into the CW-type cytoplasmic male sterile line.

The "PPR" is an abbreviation for "pentatricopeptide repeat" that is protein having a repeated conserved sequence consisting of 35 amino acids. The protein is considered to bond to the RNA of arganelle and be involved in RNA processing and regulation of translation.

EXAMPLE 2

Restoration of the Fertility by Expression of the Gene of SEQ ID NO:2

Figure 2:
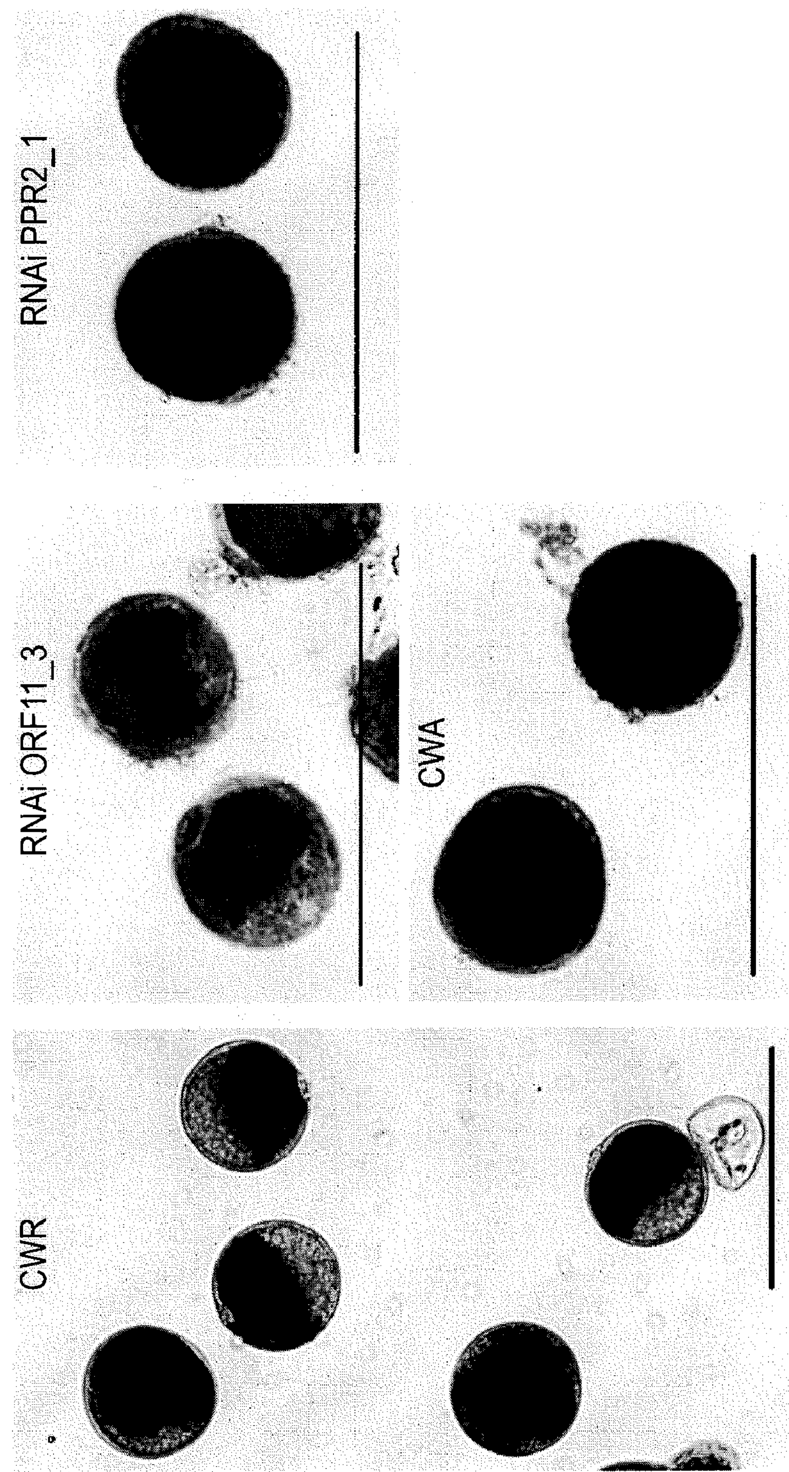
FIG. 2 Photos showing the presence or absence of decomposition of the starch of pollen in a transformed plant into which a vector inducing RNA interference has been introduced. The decomposition of starch was observed in the fertility restorer line (CWR) and an individual plant (RNAi ORF11_3) into which an RNA interference vector for ORF11 has been introduced, but it was not observed in the male sterile line (CWA) and an individual plant (RNAi PPR2_1) into which an RNA interference vector for PPR2 has been introduced.

Mapping of the fertility restorer gene, Rf17, for the CW-type CMS line revealed 14 candidate genes within the candidate region of 77 kb. According to polymorphism analysis of the CMS line and the fertility restorer (CWR) line, an amino acid mutation had occurred only in the PPR gene ("PPR2 gene" in FIG. 1) and the stop codon was generated in an allele of the CWR line. According to expression analysis done for each of the 14 candidate genes, only ORF 11 gene showed the difference between the CMS line and the CWR line. The base sequence comprising a coding region, and its 5'- and 3'-non translation regions are shown as SEQ ID NO:2. A base sequence corresponding to that at the 638-815 positions of the base sequence represented by SEQ ID NO:2 (its first base is numbered as "1 position") and a base sequence corresponding to that at the 772-1505 positions of the base sequence represented by SEQ ID NO:1 (its first base is numbered as "1 position"), which corresponds to PPR2 gene, were amplified by means of PCR using the primers represented by SEQ ID NO:3 and NO:4, and the primers represented by SEQ ID NO:5 and NO:6, respectively, and linked down stream of a ubiquinone promoter of pANDA vector to give a vector that induces the RNA interference. The resulting vectors were introduced into the CW-type CMS line by means of *Agrobacterium* method, and shape of pollen and seed fertility were investigated. As a result, the expression of ORF11 was reduced down to 30-77% in seven (7) lines into which the RNA interference-inducing vector for ORF11 had been introduced. And, four (4) lines out of said seven lines showed decomposition of the starch of pollen, which is characteristic to the fertility restorer line (FIG. 2), and their seed fertility was partially restored (2-3%). On the other hand, although the expression of ORF11 was reduced down to 27-75% in six (6) lines into which the RNA interference-inducing vector for PPR2 had been introduced, no decomposition of the starch of pollen was observed like the CMS line (FIG. 2) showing the seed fertility of 0%. The above results demonstrated that the fertility of the CW-type CMS line can be restored by inhibiting or reducing the expression of the gene ORF11.

EXAMPLE 3

Determination of Rf17 Genotype

Figure 3:
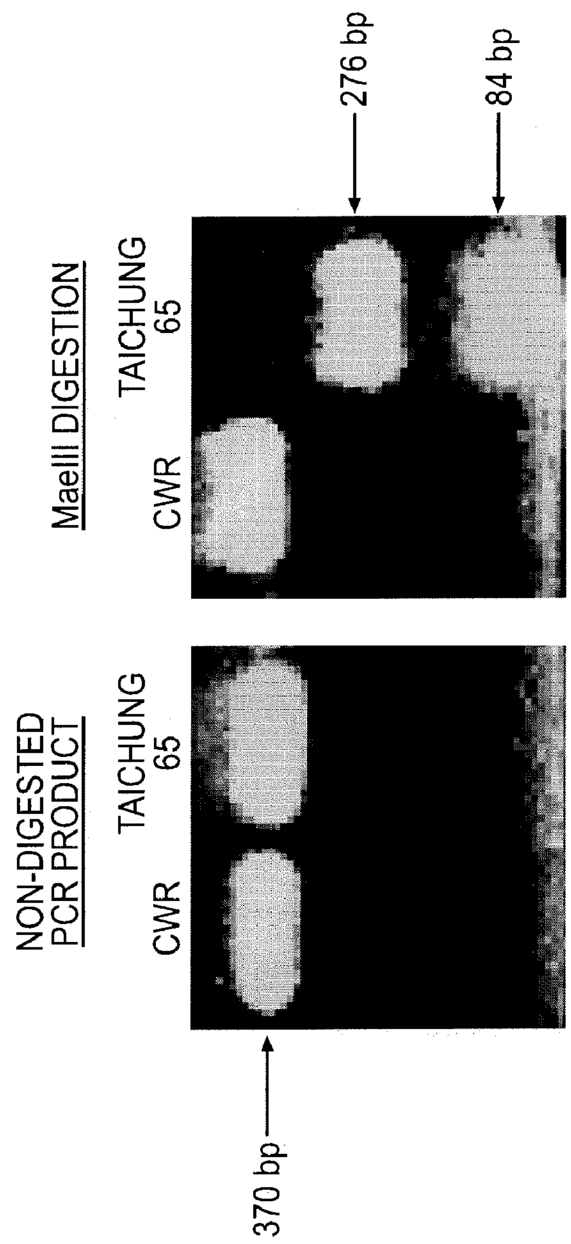
FIG. 3 Photos of electrophoresis showing the determination of the Rf17 genotype by means of PCR with a CAPS marker. While the fertility restorer line (CWR) generated a band of 370 bp, a variety having no fertility restorer capability (Taichung 65: T65) generated bands with 276 bp and 84 bp.

Comparison of the base sequences represented by SEQ ID NO:1 comprising the fertility restorer gene Rf17 with that of Nipponbare-type rice revealed that a base at the 1812 position of the base sequence represented by SEQ ID NO:1 is "T" in the fertility restorer (CWR) line, while "A" in the nipponbare-type rice that has no fertility-restoring capacity. A CAPS marker was prepared for a simple identification of this mutation. PCR was carried out using two primers represented by SEQ ID NO:7 and NO:8. Treatment with a restriction enzyme MaeIII and electrophoresis gave a band with 370 bp in the fertility restorer line (CWR), and bands with 276 bp and 84 bp in the nipponbare-type rice (FIG. 3). The above results showed that the present or absence of Rf17 could be simply determined By the way, the restriction enzyme that can be used in the above determination is not limited to MaeIII, but any restriction enzyme may be used as long as it recognizes the cleavage site GT(A)AAC.

INDUSTRIAL APPLICABILITY

According to the present invention, a hybrid variety can be bred by the three-line method using the CW-type male sterile cytoplasm.

What is claimed:

1. A kit used for determining the presence or absence of gene Rf17, comprising:

at least one PCR primer capable of hybridizing to SEQ ID NO:1 that is so designed to form a PCR product wherein a restriction enzyme-recognition site will be formed at the position corresponding to the 1812 position of the base sequence represented by SEQ ID NO:1, and a restriction enzyme that recognizes a cleavage site having a base sequence of GTAAC, where a single nucleotide polymorphism (SNP) exists.

2. The kit according to claim 1, wherein the at least one PCR primer comprises SEQ ID NO:7 or SEQ ID NO:8.

3. The kit according to claim 1, wherein a first PCR primer comprises a base sequence represented by SEQ ID NO:7 and a second PCR primer comprises a base sequence represented by SEQ ID NO:8.

4. The kit according to claim 1 wherein the restriction enzyme is MaeIII.

5. A method for detecting a single nucleotide polymorphism (SNP) in the gene Rf17 of rice, which is a fertility restorer gene for the CW-type cytoplasmic male sterility, comprising identifying a SNP in a base at the 1812 position of SEQ ID NO:1, the method comprising the steps of:

using at least one PCR primer capable of hybridizing to SEQ ID NO:1 to form a PCR product wherein a restriction enzyme-recognition site will be formed at the position corresponding to the 1812 position of the base sequence represented by SEQ ID NO:1, and cleaving the amplified product at said position using a restriction enzyme that recognizes a cleavage site having a base sequence of GTAAC.

6. The method according to claim 5, wherein the restriction enzyme is MaeIII.

* * * * *

SEQUENCE LISTING

```
<160> NUMBER OF SEQ ID NOS: 8

<210> SEQ ID NO 1
```

```
<211> LENGTH: 4871
<212> TYPE: DNA
<213> ORGANISM: Rice
<220> FEATURE:
<223> OTHER INFORMATION: Genome fragment No.5 derived from chromosome
      No.4

<400> SEQUENCE: 1

ggatccggca gctcttcacc attctcttca accttcaagc cttcatgaaa tgctccacaa     60

tttgttgact gttgattaga aataggaaat ttagaagaag aaaaaaaaat actccacatg    120

agcttgaaaa atgtaacatg cagttttgaa atcaacctca tggcccacag tacttgagct    180

aaagagatga cggtgcagtt caacaacaaa gaatacacat caggggggaa tggtggtgca    240

cctaaaattt taggtgtttg ggaattgaaa tatcaccact caatgactat ggttcaatga    300

gataattact gcacaaatta ttggtcatta ttggacgatg taccaaaaca gtcaagagca    360

tatccactgg ttgcagaata gtaccacaaa tgaagtataa atctccgtgt atatgcaatc    420

ttaatcttcc caatcatatg atcagtacaa tcaacaggta taaaatttag aaattttatt    480

tggattgggt gtggaaaagg tcaaccaggt aactgcatga ccatagatgt aactgtaatc    540

tgaagttctg aacagtacct taatcatcaa attattgacc atggaattac tgcaagcgca    600

acagaccttg acatccaact gagcccaata atctgacttc ctttaaggcc aaaccaaaga    660

atggatgcta caatcctaca agcttgctta gcccagcaac aagagaagac caaccataaa    720

atttgctgat gtcctcaagt accatgcaca aacagtaggc tgccctgaat tcgcagactc    780

tcaacaaggt taacactttc agcaaacttc ccacatttgt gaaagtaccg gagtaagcat    840

gtcatactga tggcatcaag gttgattcct tccacatgca tacgatagag aaccatacgg    900

ataactgaag cattctgctg cctgcaggct gcagagagga tagtgttgaa ggagactgaa    960

tcacagggaa caccagtaga gctaaaatgg tccaacatct gcaatgcccc ctgaagatcc   1020

agctccatac agaagccttt cagtatagtg ttatatgttg tagtagatgg tacaagtcct   1080

ctctccatca ttccactaac caaagctaat gctttcttaa cctgcccatc acagcataag   1140

ctatggaggt atatattcca agtgataata tccacatgat tgctcctgtt acataccatt   1200

cgtataaaat tctgacaggt catgacatcc ccagttttca gaaagccagc agccagagaa   1260

gaaatggtga aatagtcagg gaccaatcct gcctcctcca tcaaatcaac aatcacccga   1320

gcttctggta ttctatcttc gcagcagagt gcatggagta gcacattgca tatggtgcta   1380

tcaagacaac agccattttt gcatgccatc ctgaaaacat gcatcgcagc atcaatctta   1440

ccatctctac agaggaaatt cacaattacg gtatatgtta caacagaggg tttgcactct   1500

tcatcgcaca tcttctccaa tgccctgtat gcgtcggccc acatcttctc cttgcataat   1560

cctaagacca atgctgtata cgaataaacg tttagagaga gtcctctctt cttcaagtta   1620

cagaacagag tcaatgcctt attgctgcaa cctgacttgc aaagaccaaa cagaatttgg   1680

ttgtacatat acacatctgg cacaaacttc ctatttacaa gcaccatgaa aacctcatat   1740

gcaatctcag cgctgccact tttcaataga atcgagacaa tggcattggc gatagggaga   1800

gtcggaaagt atcacagact gagcattagg tcgaacacct tcagtgcaag ttcaaagtta   1860

gagccactaa cagctttctt gatgagtcta tctaccgtgg tgaacgaagg cacgaatccg   1920

cagcgagacc acatctcttc gagtaccgcg tgcgaggcgt cgaggtggcc tagccggagc   1980

agcccgttga aggcggtatt gaaggtgagg gcgttgggcg ccgggccgac ggagcgcatg   2040

tgacacagca cggcggctac atgctccgcg gcggcgacgt gttgcgcggc ggcttgcccg   2100

gaccggaggt aggcgtggag gagggcgttg tagtcgtggg cgcctgcggg cgcgggccgg   2160
```

-continued

```
aggagggcga gcgcgtccag cgccgcggcc aggttcccct cggcggccga cgcccgcatg   2220
cggcggcgga ggagcgtggc atccgcgggg ccgtgggatt cggggtccac gtcggagtcg   2280
gaggtggaaa tggaagcttc gacgggggag gcggcggcgg tggcgagagc ggagcggaag   2340
cgcaggcgga cgcggcggca tgaggcgagc ataggatggg gggcagttcc taccagctgc   2400
gatgtgatgt tcgattcatg aggaggacgg tgatgccgga ggcggaggtg gtggtggtgg   2460
ttgggcggcg ccgccgacgc gcgggctgtg gaggagcggt ggcggcgccg acggtggcgg   2520
agggaggcag gaagcggcgt gtggaggagg aggcggcggc gccgcgtcgc gcgtcggcgt   2580
gtgggcgtgg aggaggcgga ctggcggttg ctgggctgga tggttaggtt tttcggttaa   2640
ttgtctaatt gatgggctga atgggccagt atagtgtgtc ttatggccga ataaaatgga   2700
ataagttcat cataggtccc ttaaccgaat ccgattttcg tccttcaact ggaaaaccag   2760
atcgggtccc tcaactatca cacccggtgc agatgaggtc cctcagcgtt ttagatggcg   2820
gttttggcag acgtgacgct tagtggctag tttgtctctg tcttcatctg acgtgacgct   2880
tacgtggcaa ttcgaaccgg aaaagtaata aaactcgtgg gacccacgga tcagtttcac   2940
acataaacta ataaaaaata gtgagcccca catgtcatcc tcactccctt cttccctcta   3000
tcccctctct ctcttcttcc ctacaatgtg gactggggcg gcgggcggac gagcgcaacc   3060
gcggccgaag cagcagcgca cgaagccgac ggggcggtgg caatcctccg ccgacgccga   3120
tatccacagc agaggtgcgc gtcctcctcc tccttaaacc cgtcaccatc ggtggccgtc   3180
cccccctgggc ctccgcccgc ggctcctctc cttccgtcgg ccggcaagca agatacacaa   3240
acaattagca gaaaggccga ccctatcggc atcggcaagc attccccgat ccaagctagc   3300
ttctaccaaa catcgactca gtggatctca aggatgtgtc cgaccagcca gattttactt   3360
aggcctccat ccaaacagtc tctaaaacca ccttctacct atggcctgtt tggcacagct   3420
ccagctccac ccctcctgga gctagagctc agccaaacag ttttagctcc accaaaactg   3480
agagtggagc taggtggagc tctctcacaa aatgaactag agttgttgag ctgggtttag   3540
gcagctccac aactttactc cagacccaac ttctagagct aaatttagga gttggagcta   3600
aattgagggc ttgttaaatt tgtttggttt aaataattaa aaatgtcaaa tgtctggtcg   3660
tgtaattcgg atcaggagcg aatccagaaa atgaatggta ggagggcttg tctcattcct   3720
cctctaaggg catctccaac agcttcccca aatcgaactc tccaaacact catatagcca   3780
actctccatc tgatttagct agtcaaatta gatactcact ccaacagact ctctattaat   3840
cctctccaaa ataaaaatag accctcagcc tctaccatct tctttctctc tctcccccca   3900
ccttccttct ctttccttct ttttcccctt ttccttcctt cccgtcgacc acgttgatgc   3960
cgacggtggc tgacacatga cgcgcggtgg tgcagcaacg cggggaggcg gaaggcggtg   4020
cggggaggcg gcgctcgctg aggtgctctc cctctccctt tgcggcgacg aggcgacggc   4080
ggcggagctc ggagcgggat ggcgatggcg gcggcggagc tcggggtggg gatggcaaag   4140
gcggcggctc tccacaacga cgacttggcg aggcgacgac gacggcgagg aagatgcagc   4200
cacgacagca catgggcagg gatggcactg gaggcacatg gcggccacgg cgacggagtc   4260
gagggagagg cgcgggaagc cgcaaggggt ggccctctgc tcctcgccgg ccttgcctgg   4320
tcctccgccg ccttgtcgcc gtggctccgc tggttccggg aggcaggggc gagagagagg   4380
agggagggag tgaggtggag cgcggggact cggttccagg cgatggtgga agggggacgg   4440
caggggaggc agggcaaaag aggcgctcgc gcctccggtc catttcggcg gagggcggcg   4500
atggaagcag ccgaggcagc gttgaagagt ttggggacag agagaatgcg agatgtggga   4560
```

agaaaaatat ggttgtgggt cccacaatcc cacagttgga gagccagttt tggctggcca 4620
agtttagcca cctagggagc ccctttggcc aaccaaatag cttcgagagt aggatagcca 4680
gtatgttgga gctcgttttt tttttcaaaa tttctaaatt ttagtttggg gagtgaaata 4740
gctatgctgt tagagatgct ctaagcccct actcttttc tccctcttct tcctcctccc 4800
atatctccct ttctcttaat ggtcattcag cggggtaggg ggcttgagct cctagcacct 4860
acgctggatc c 4871

<210> SEQ ID NO 2
<211> LENGTH: 854
<212> TYPE: DNA
<213> ORGANISM: Rice
<220> FEATURE:
<223> OTHER INFORMATION: Fragment comprising ORF11 gene

<400> SEQUENCE: 2
tctttctctc tctcccccca ccttccttct ctttccttct ttttcccctt ttccttcctt 60
cccgtcgacc acgttgatgc cgacggtggc tgacacatga cgcgcggtgg tgcagcaacg 120
cggggaggcg gaaggcggtg cggggaggcg gcgctcgctg aggtgctctc cctctccctt 180
tgcggcgacg aggcgacggc ggcggagctc ggagcgggat ggcgatggcg gcggcggagc 240
tcggggtggg gatggcaaag gcggcggctc tccacaacga cgacttggcg aggcgacgac 300
gacggcgagg aagatgcagc cacgacagca catgggcagg gatggcactg gaggcacatg 360
gcggccacgg cgacggagtc gagggagagg cgcgggaagc cgcaaggggt ggccctctgc 420
tcctcgccgg ccttgcctgg tcctccgccg ccttgtcgcc gtggctccgc tggttccggg 480
aggcaggggc gagagagagg agggagggag tgaggtggag cgcggggact cggttccagg 540
cgatggtgga agggggacgg caggggaggc agggcaaaag aggcgctcgc gcctccggtc 600
catttcggcg gagggcggcg atggaagcag ccgaggcagc gttgaagagt ttggggacag 660
agagaatgcg agatgtggga agaaaaatat ggttgtgggt cccacaatcc cacagttgga 720
gagccagttt tggctggcca agtttagcca cctagggagc ccctttggcc aaccaaatag 780
cttcgagagt aggatagcca gtatgttgga gctcgttttt tttttcaaaa tttctaaatt 840
ttagtttggg gagt 854

<210> SEQ ID NO 3
<211> LENGTH: 24
<212> TYPE: DNA
<213> ORGANISM: Artificial Seqeunce
<220> FEATURE:
<223> OTHER INFORMATION: Primer for the construction of RNA interference vector of ORF11

<400> SEQUENCE: 3
caccagcgtt gaagagtttg ggga 24

<210> SEQ ID NO 4
<211> LENGTH: 20
<212> TYPE: DNA
<213> ORGANISM: Artificial Sequence
<220> FEATURE:
<223> OTHER INFORMATION: Primer for the construction of RNA interference vector of ORF11

<400> SEQUENCE: 4
cgagctccaa catactggct 20

-continued

```
<210> SEQ ID NO 5
<211> LENGTH: 24
<212> TYPE: DNA
<213> ORGANISM: Artificial Sequence
<220> FEATURE:
<223> OTHER INFORMATION: Primer for the constrcution of RNA interference
      vector of PPR2

<400> SEQUENCE: 5

cacctgaaga gtgcaaaccc tctg                                            24


<210> SEQ ID NO 6
<211> LENGTH: 20
<212> TYPE: DNA
<213> ORGANISM: Artificial Sequence
<220> FEATURE:
<223> OTHER INFORMATION: Primer for the constrcution of RNA interference
      vector of PPR2

<400> SEQUENCE: 6

ttcgcagact ctcaacaagg                                                 20


<210> SEQ ID NO 7
<211> LENGTH: 26
<212> TYPE: DNA
<213> ORGANISM: Artificial Sequence
<220> FEATURE:
<223> OTHER INFORMATION: Primer for determination of Rf17 gene type

<400> SEQUENCE: 7

tcgttcacca cggtagatag actcat                                          26


<210> SEQ ID NO 8
<211> LENGTH: 25
<212> TYPE: DNA
<213> ORGANISM: Artificial Sequence
<220> FEATURE:
<223> OTHER INFORMATION: Primer for determination of Rf17 gene type

<400> SEQUENCE: 8

cccacatctt ctccttgcat aatcc                                           25
```